US012642983B2

(12) United States Patent
Swanson et al.

(10) Patent No.: US 12,642,983 B2
(45) Date of Patent: Jun. 2, 2026

(54) PHOTOTHERAPY SYSTEMS, METHODS OF USING A PHOTOTHERAPY SYSTEM, AND METHODS OF MANUFACTURING A PHOTOTHERAPY SYSTEM

(71) Applicant: The Daavlin Distributing Co., Bryan, OH (US)

(72) Inventors: David Swanson, Bryan, OH (US); Robert Golding, Bryan, OH (US)

(73) Assignee: The Daavlin Distributing Co.

( * ) Notice: Subject to any disclaimer, the term of this patent is extended or adjusted under 35 U.S.C. 154(b) by 407 days.

(21) Appl. No.: 17/397,078

(22) Filed: Aug. 9, 2021

(65) Prior Publication Data

US 2022/0040493 A1     Feb. 10, 2022

Related U.S. Application Data

(60) Provisional application No. 63/063,573, filed on Aug. 10, 2020.

(51) Int. Cl.
A61N 5/06          (2006.01)

(52) U.S. Cl.
CPC ........ A61N 5/06 (2013.01); *A61N 2005/0652* (2013.01); *A61N 2005/0661* (2013.01)

(58) Field of Classification Search
CPC ..................... A61N 5/06; A61N 5/0616; A61N 2005/0644; A61N 2005/0652; A61N 2005/0654; A61N 2005/0661
See application file for complete search history.

(56) References Cited

U.S. PATENT DOCUMENTS

| | | | |
|---|---|---|---|
| 8,486,124 B2 | 7/2013 | Hendrix et al. | |
| 9,901,747 B2 | 2/2018 | Gamelin et al. | |
| 9,913,993 B2 | 3/2018 | Gross et al. | |
| 2002/0111610 A1* | 8/2002 | Nordquist ............ | A61N 5/0616 606/11 |

(Continued)

FOREIGN PATENT DOCUMENTS

| | | | |
|---|---|---|---|
| WO | 03047682 A2 | 6/2003 | |
| WO | 2008088792 A1 | 7/2008 | |

OTHER PUBLICATIONS

PCT International Search Report and Written Opinion, Application No. PCT/US2021/045165, dated Jan. 25, 2022.

(Continued)

*Primary Examiner* — Pamela M. Bays
*Assistant Examiner* — Shreya Anjaria
(74) *Attorney, Agent, or Firm* — MacMillan, Sobanski & Todd, LLC

(57) ABSTRACT

Example phototherapy systems, methods of using a phototherapy system, and methods of manufacturing a phototherapy system are described. An example phototherapy system includes a handle and a phototherapy light source. The phototherapy light source is attached to the handle, adapted to emit a light in a therapeutic wavelength, and includes a plasma lamp. The plasma lamp can be disposed between sheets of transparent material, including quartz. The phototherapy light source can be adapted to emit a light in a UVB wavelength between about 300 nanometers and about 320 nanometers and can have an output of between about 15 mW/cm$^2$ and about 21 mW/cm$^2$.

16 Claims, 18 Drawing Sheets

(56)                    References Cited

U.S. PATENT DOCUMENTS

| | | | |
|---|---|---|---|
| 2005/0143793 A1* | 6/2005 | Korman ............... | A61N 5/0616 |
| | | | 607/94 |
| 2007/0038206 A1* | 2/2007 | Altshuler ........... | A46B 15/0036 |
| | | | 606/20 |
| 2008/0172112 A1* | 7/2008 | Gourgouliatos ..... | A61N 5/0617 |
| | | | 607/94 |
| 2010/0179622 A1* | 7/2010 | Wagenaar Cacciola ..................... | |
| | | | A61N 5/0616 |
| | | | 607/94 |
| 2014/0209945 A1* | 7/2014 | Baldridge ............. | H01L 27/153 |
| | | | 257/91 |
| 2015/0217130 A1 | 8/2015 | Gross et al. | |
| 2017/0182282 A1* | 6/2017 | Rea ........................ | A61G 11/00 |
| 2018/0111002 A1 | 4/2018 | Gamelin et al. | |
| 2018/0117355 A1* | 5/2018 | Loupis ................. | A61N 5/0616 |
| 2018/0147415 A1 | 5/2018 | Gross et al. | |
| 2018/0178032 A1* | 6/2018 | Pilcher ................. | A61N 5/0616 |
| 2023/0012145 A1* | 1/2023 | Moreira Guimarães .................... | |
| | | | A61N 5/0616 |

OTHER PUBLICATIONS

International Preliminary Report on Patentability, Application No. PCT/US2021/045165, dated Feb. 7, 2023.
UV 2001, Daavlin Fall Brochure, 1993, pp. 1-4.

\* cited by examiner

66

68

16

18

166

168

300

302 — OBTAINING A PLURALITY OF LEDs

304 — COMPLETING SPECTRAL ANALYSIS

306 — CAMPARING CHARACTERISTICS

308 — ASSOCIATING A PREDETERMINED TREATMENT TIME

310 — INCORPORATING PLURALITY OF LEDs INTO PHOTOTHERAPY SYSTEM

PHOTOTHERAPY SYSTEMS, METHODS OF USING A PHOTOTHERAPY SYSTEM, AND METHODS OF MANUFACTURING A PHOTOTHERAPY SYSTEM

FIELD

The disclosure relates generally to the field of phototherapy systems, methods of using a phototherapy system, and methods of manufacturing a phototherapy system.

BACKGROUND

Phototherapy is a form of treatment which exposes a subject to either natural sunlight or light generated by an artificial light source to treat various conditions, such as dermatologic conditions. Exposing the subject to certain wavelengths, or ranges of wavelengths, of light, such as the UVB range, provides one form of treatment for these conditions. In some examples, existing phototherapy systems utilize light emitting diodes (LEDs) to generate light in a suitable wavelength to accomplish treatment. However, current phototherapy systems have various drawbacks, such as failing to be customized based on the specific components included in the device.

A need exists, therefore, for new and useful phototherapy systems, methods of using a phototherapy system, and methods of manufacturing a phototherapy system.

SUMMARY OF SELECTED EXAMPLE EMBODIMENTS

Various example phototherapy systems, methods of using a phototherapy system, and methods of manufacturing a phototherapy system are described herein.

An example phototherapy system includes a handle and a phototherapy light source. The phototherapy light source is attached to the handle, is adapted to emit light in a therapeutic wavelength, and comprises a plasma lamp.

Another example phototherapy system includes a handle and a phototherapy light source. The phototherapy light source is attached to the handle, is adapted to emit a light in a therapeutic wavelength, and has an on state and an off state. The phototherapy light source comprises a plurality of LEDs. Each light emitting diode (LED) of the plurality of LEDs has a predetermined treatment time based on a characteristic of each LED of the plurality of LEDs when the phototherapy light source is in the on state.

An example method of using a phototherapy system includes: obtaining a phototherapy system; positioning the phototherapy system adjacent a treatment site; moving the phototherapy system from a first, deactivated state to a second, active state; maintaining the position of the phototherapy system adjacent the treatment site for a period of time; moving the phototherapy system from the second, active state to the first, deactivated state; and removing the phototherapy system from adjacent the treatment site.

An example method of manufacturing a phototherapy system includes: obtaining a plurality of LEDs; completing a spectral analysis of each LED of the plurality of LEDs to obtain characteristics of each LED of the plurality of LEDs; comparing the characteristics of each LED of the plurality of LEDs and the characteristics required of an LED for a treatment intended to be performed; associating a predetermined treatment time to each LED of the plurality of LEDs based on the comparison of the characteristics of each LED of the plurality of LEDs and the characteristics required of an LED for a treatment intended to be performed; and incorporating the plurality of LEDs into a phototherapy system.

Additional understanding of these examples can be obtained by review of the detailed description, below, and the appended drawings.

DETAILED DESCRIPTION OF SELECTED EXAMPLES

Figure 1:
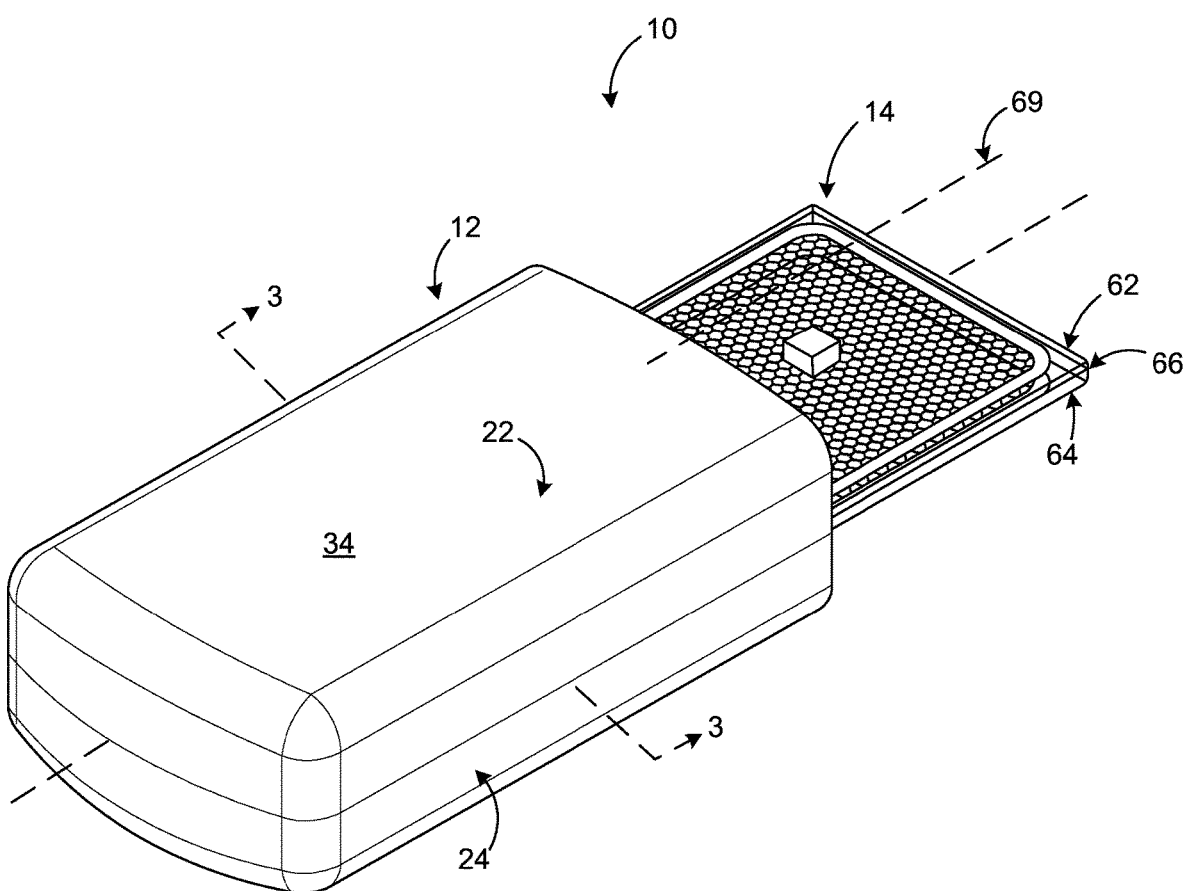
FIG. 1 is a perspective view of an example phototherapy system.
Figure 2:
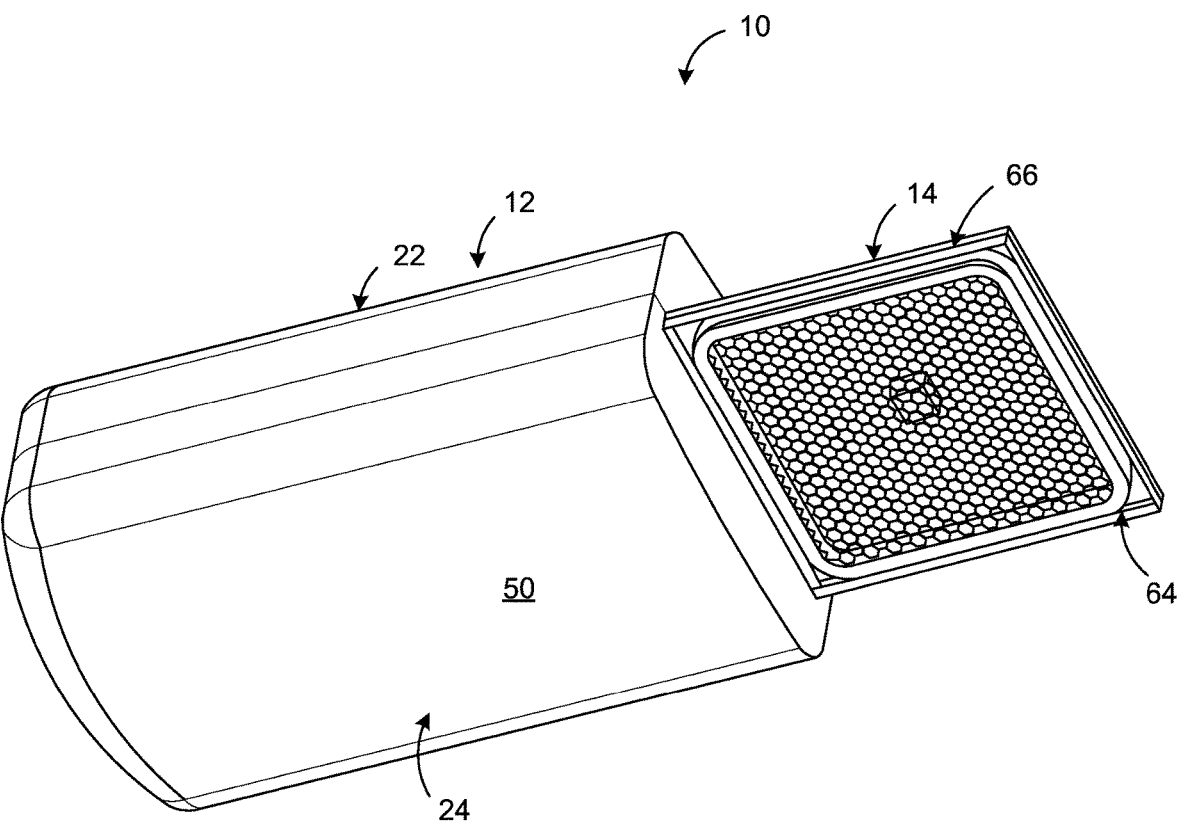
FIG. 2 is another perspective view of the phototherapy system illustrated in FIG. 1.
Figure 3:
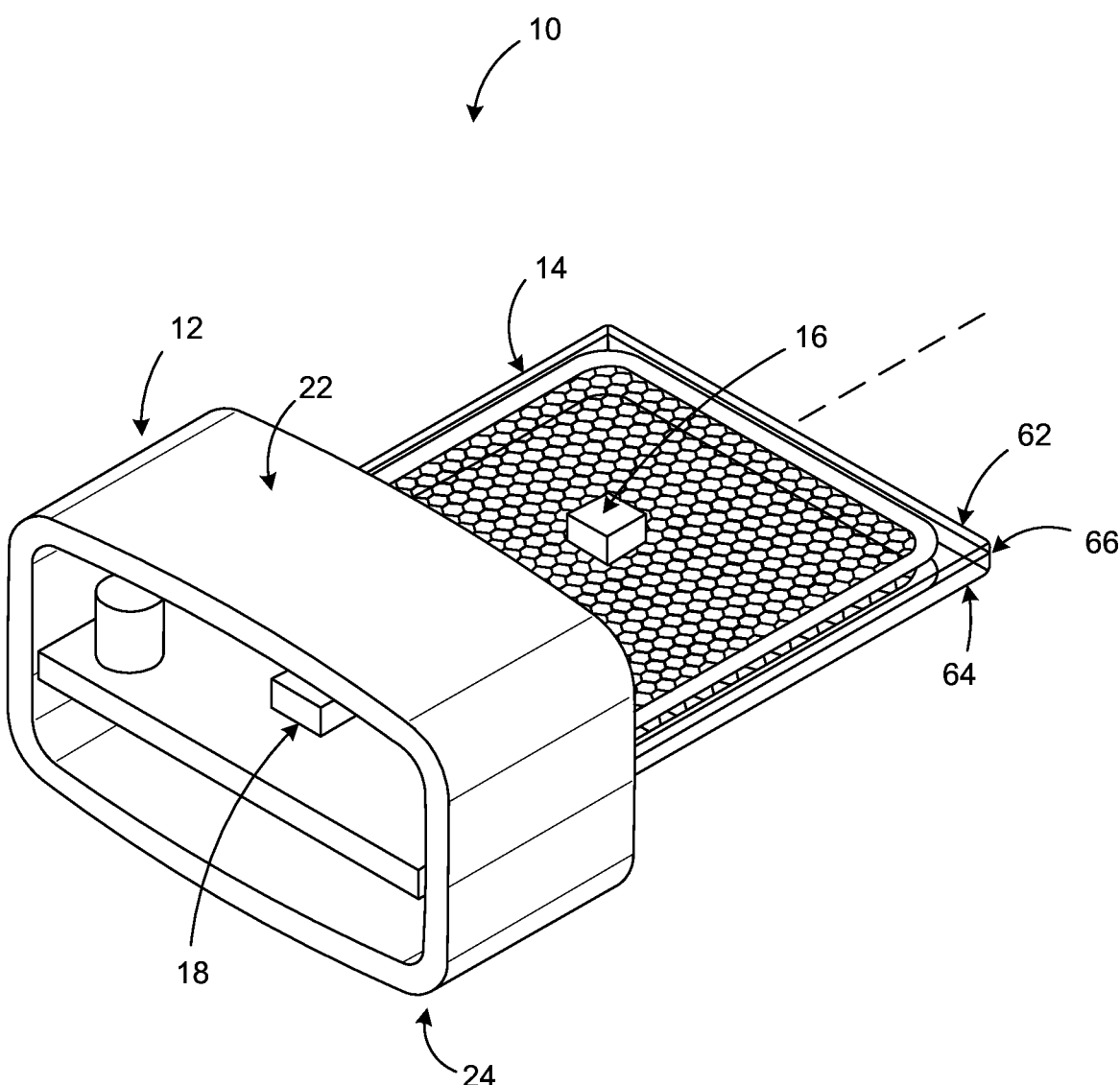
FIG. 3 is a cross-sectional view of the phototherapy system illustrated in FIG. 1 taken along line 3-3.
Figure 4:
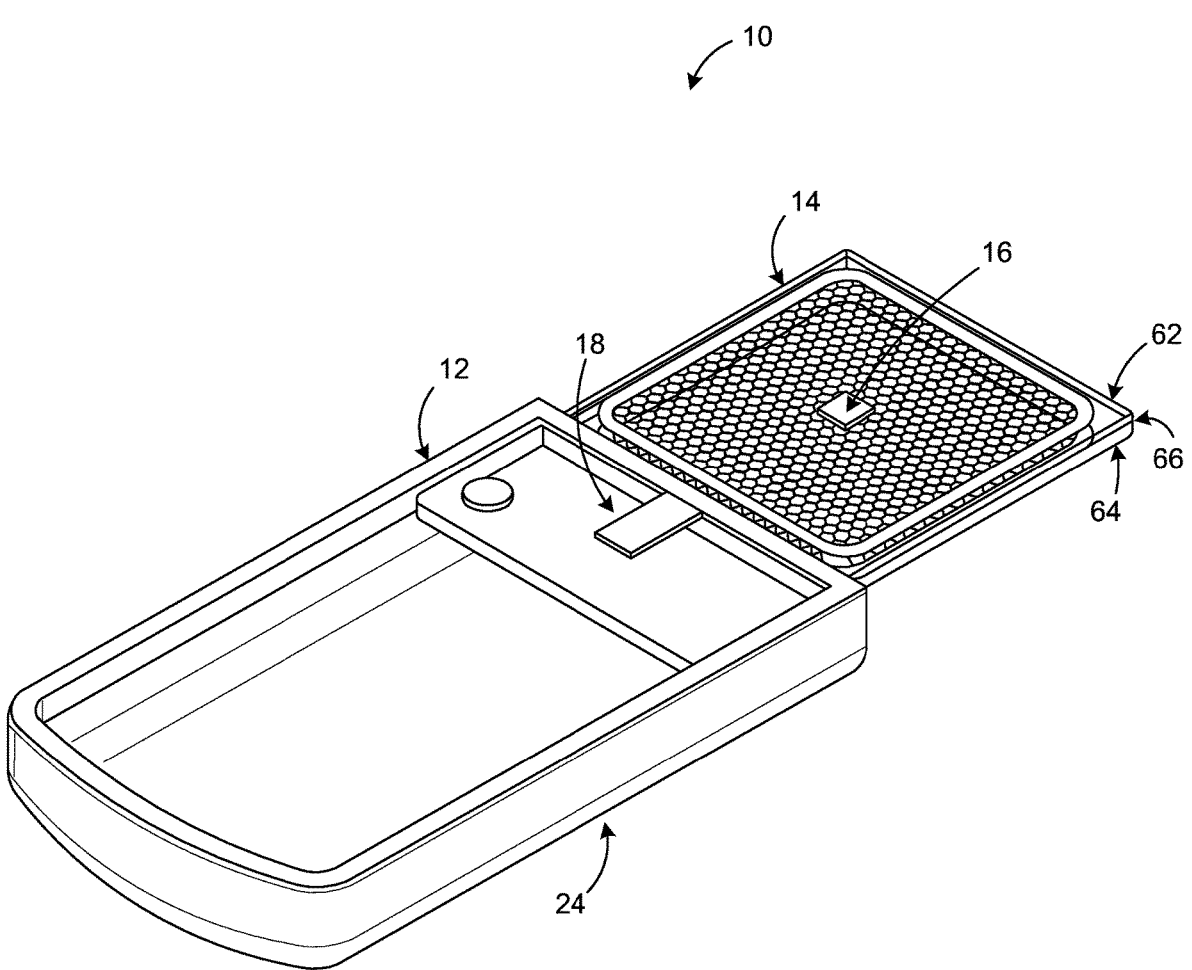
FIG. 4 is a cross-sectional view of the phototherapy system illustrated in FIG. 1 taken along the lengthwise axis of the phototherapy system.

The following detailed description and the appended drawings describe and illustrate various example embodiments of phototherapy systems, methods of using a phototherapy system, and methods of manufacturing a phototherapy system. The description and illustration of these examples are provided to enable one skilled in the art to make and use a phototherapy system, to practice a method of using a phototherapy system, and to manufacture a phototherapy system. They are not intended to limit the scope of the claims in any manner.

FIGS. 1, 2, 3, 4, 5, 6, 7, 8, 9, and 10 illustrate an example phototherapy system 10. The phototherapy system 10 has a handle 12, a phototherapy light source 14, a camera 16, and a positioning sensor 18. The phototherapy system 10 has a first, deactivated state and a second, active state.

Figure 5:
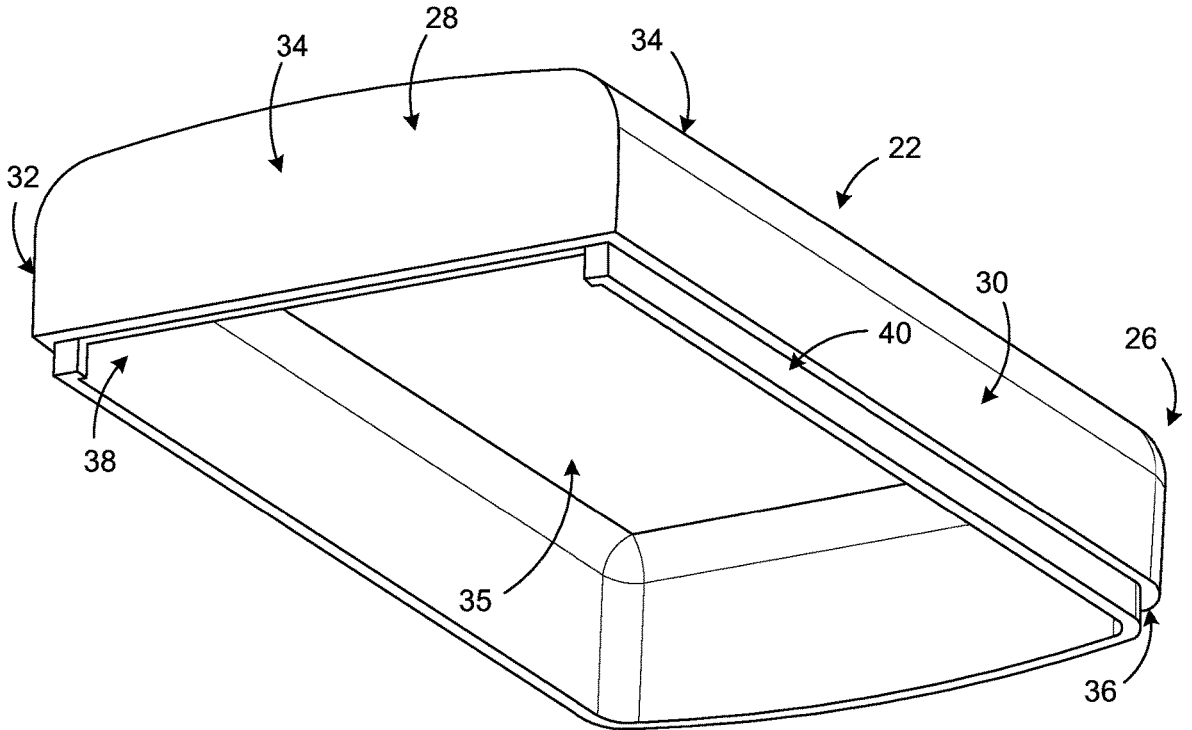
FIG. 5 is a perspective view of the first portion of the handle of the phototherapy system illustrated in FIG. 1.

In the illustrated embodiment, the handle 12 has a first portion 22 attached to a second portion 24. As shown in FIG. 5, the first portion 22 of the handle 12 has a first end 26, a second end 28, a first side 30, a second side 32, a top surface 34, a bottom surface 36, and a main body 34 that defines a recess 35, an opening 38, and a projection 40. The recess 35 extends from the bottom surface 36 toward the top surface 34 and is sized and configured to house a portion of the phototherapy light source 14 and any other components considered suitable to utilize with a phototherapy system. The opening 38 is defined on the second end 28 and extends from the second end 28 toward the first end 26 to the recess 35. The opening 38 is sized and configured to receive a portion of the phototherapy light source 14. The projection 40 extends from the bottom surface 36 away the top surface 38, around a portion of the perimeter of the main body 34, and is sized and configured to be received within the second recess 58 defined by the second portion 24 of the handle 12.

Figure 6:
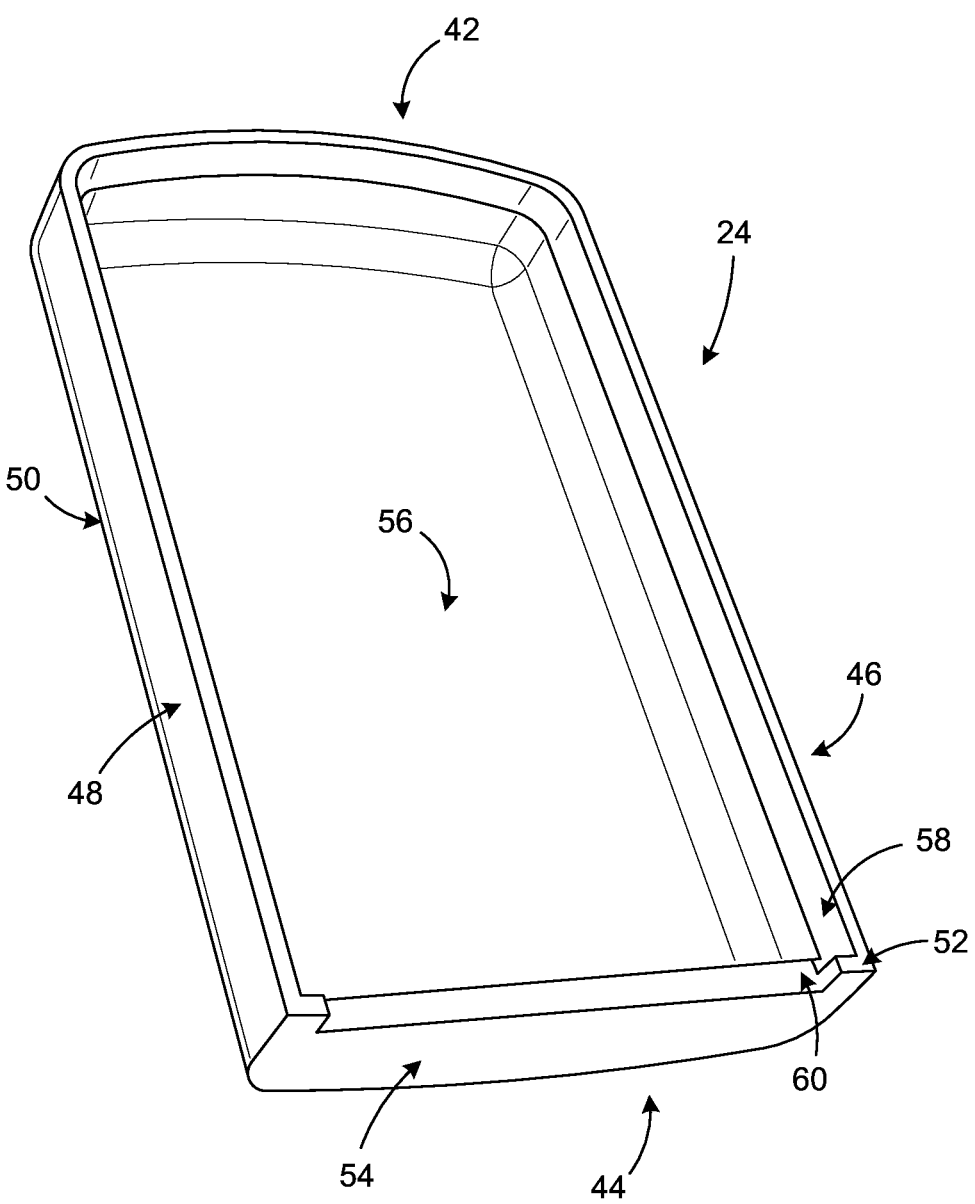
FIG. 6 is a perspective view of the second portion of the handle of the phototherapy system illustrated in FIG. 1.
Figure 7:
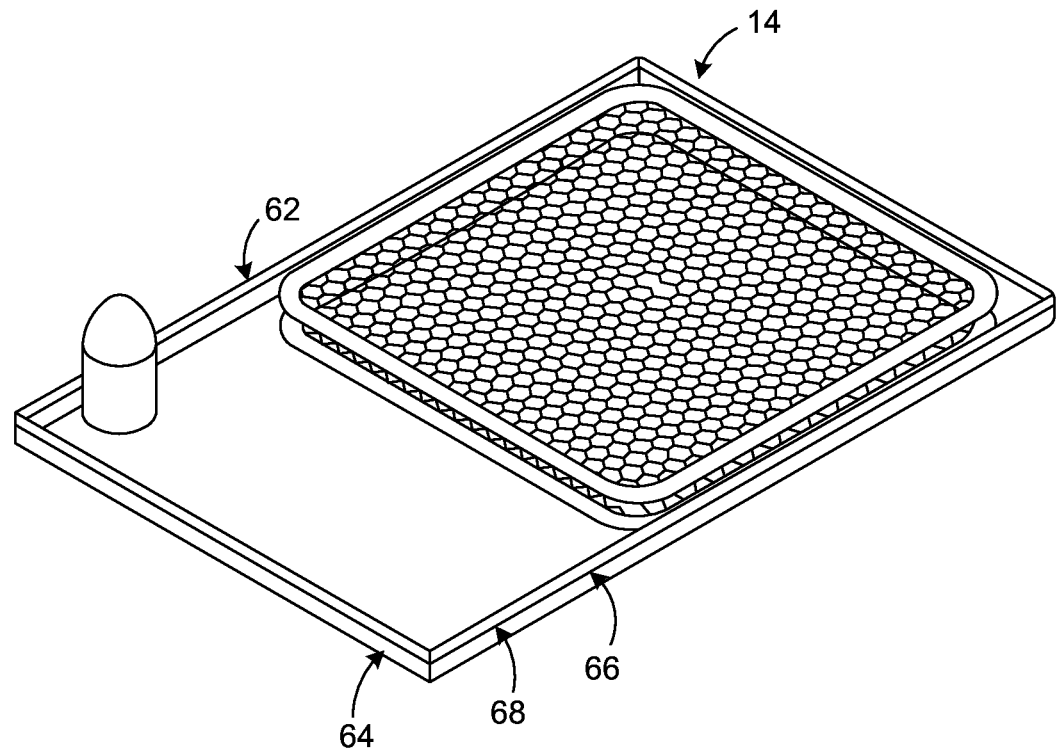
FIG. 7 is a perspective view of the phototherapy light source of the phototherapy system illustrated in FIG. 1.
Figure 8:
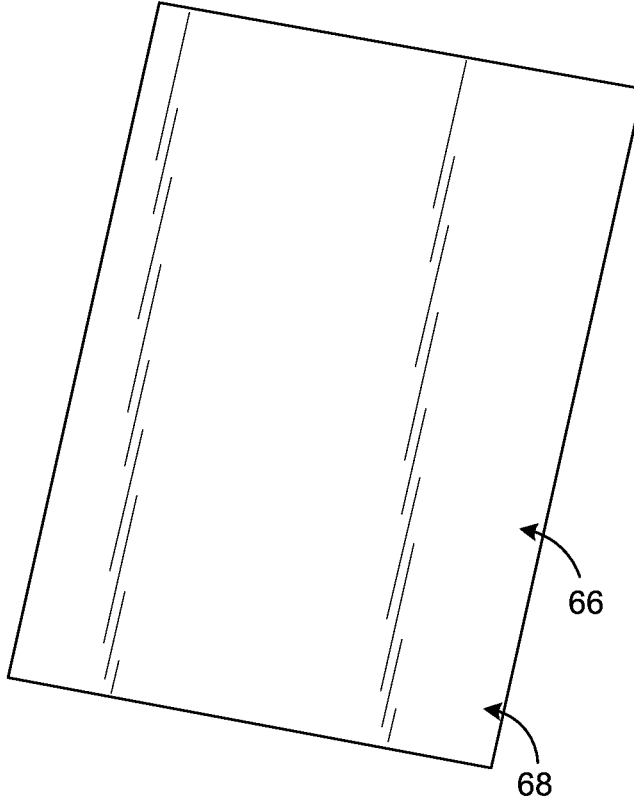
FIG. 8 is a perspective view of the lamp of the phototherapy system illustrated in FIG. 1.
Figure 9:
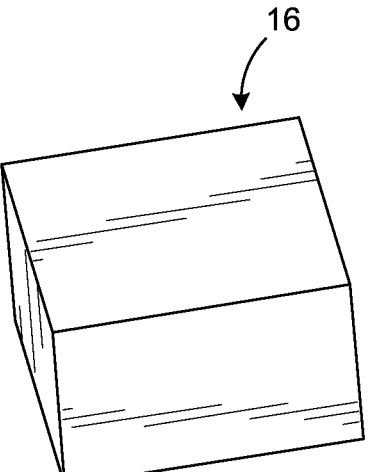
FIG. 9 is a perspective view of the imaging device of the phototherapy system illustrated in FIG. 1.
Figure 10:
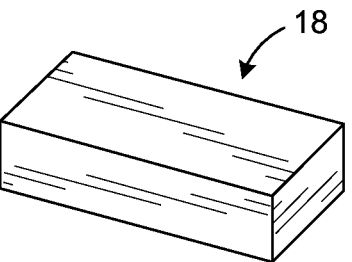
FIG. 10 is a perspective view of the positioning sensor of the phototherapy system illustrated in FIG. 1.
Figure 11:
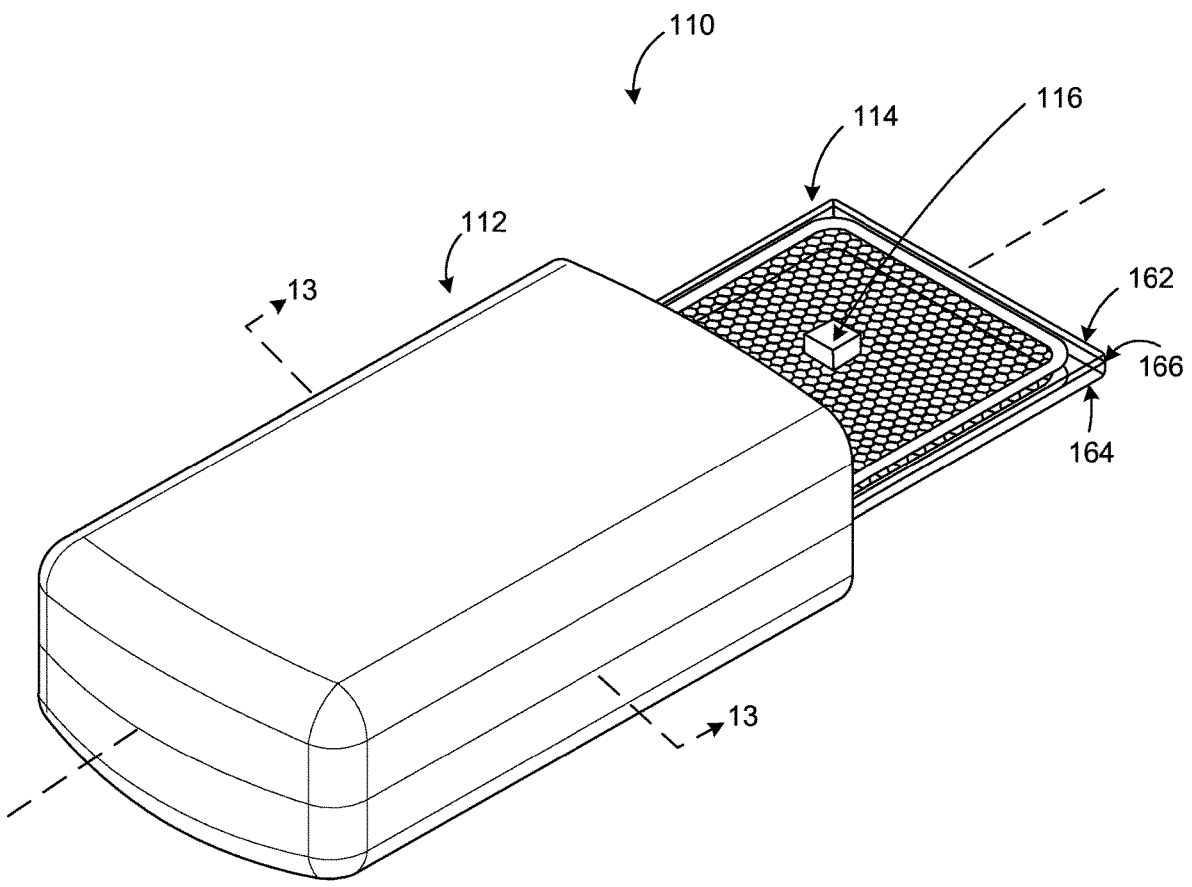
FIG. 11 is a perspective view of another example phototherapy system.
Figure 12:
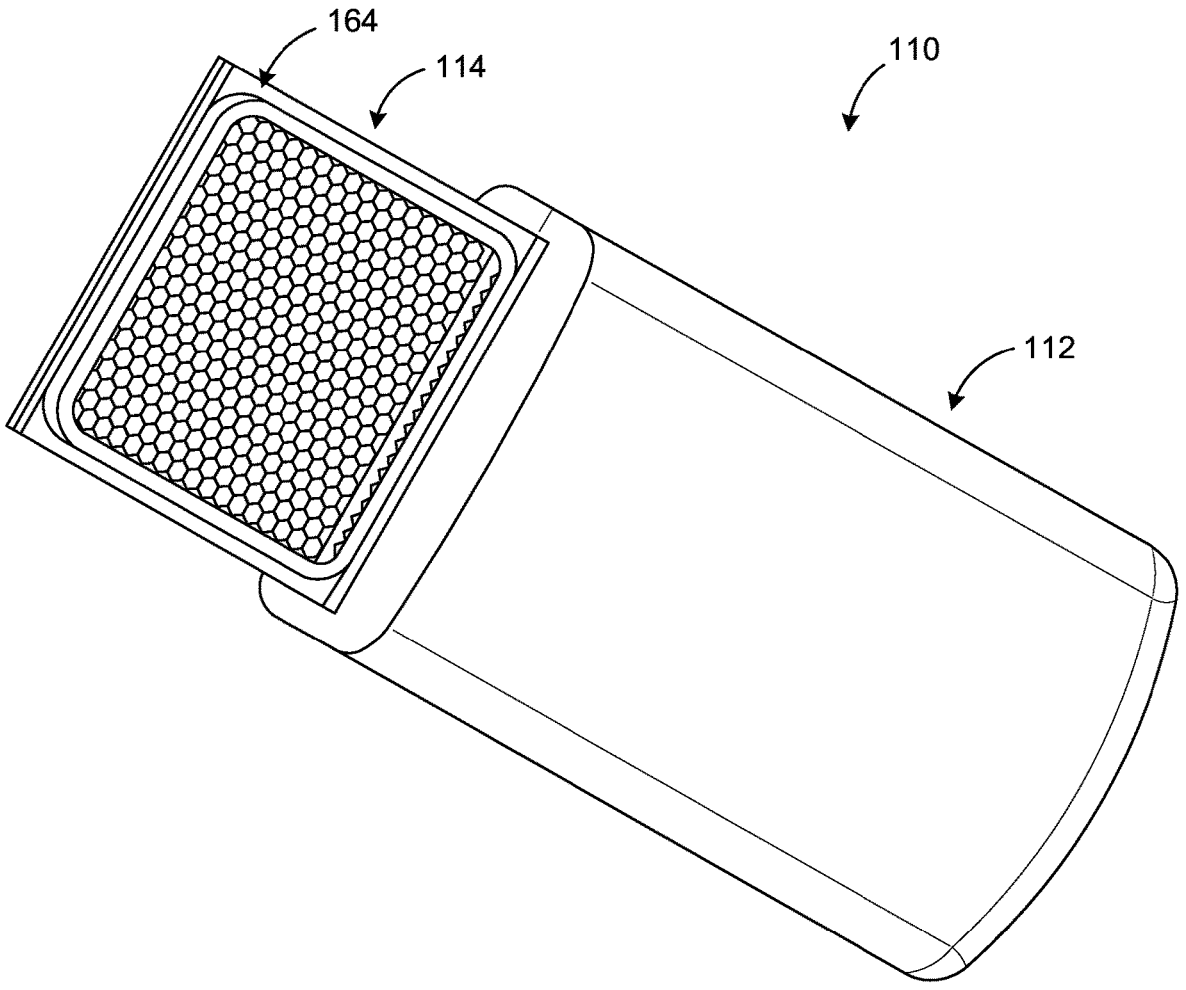
FIG. 12 is another perspective view of the phototherapy system illustrated in FIG. 11.
Figure 13:
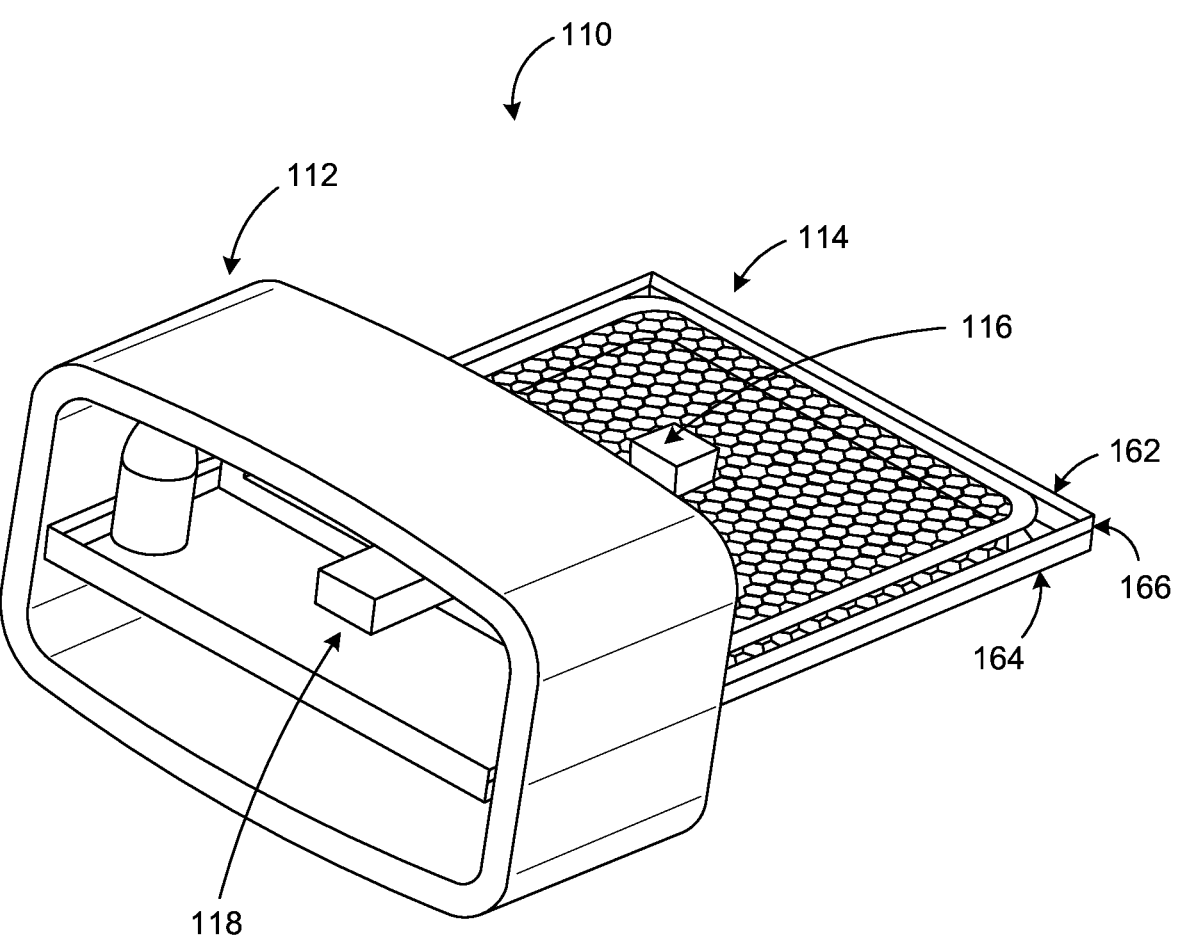
FIG. 13 is a cross-sectional view of the phototherapy system illustrated in FIG. 11 taken along line 13-13.
Figure 14:
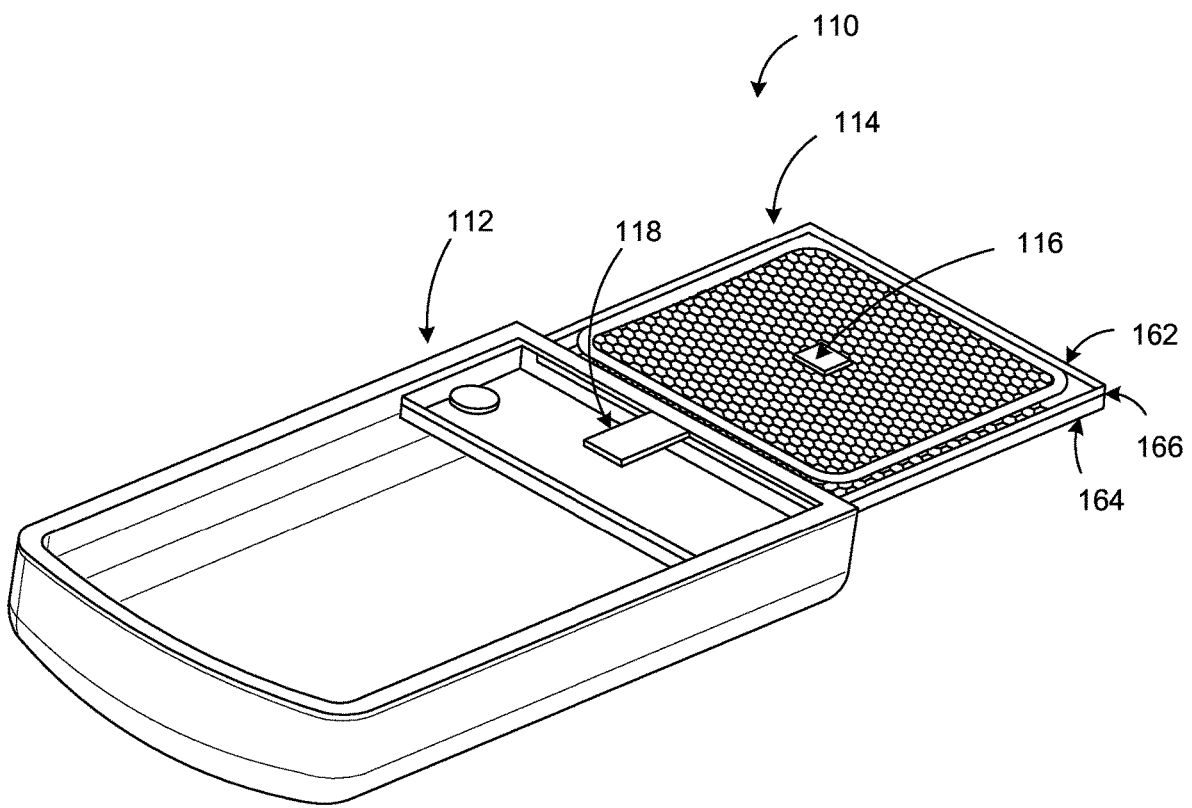
FIG. 14 is a cross-sectional view of the phototherapy system illustrated in FIG. 11 taken along the lengthwise axis of the phototherapy system.
Figure 15:
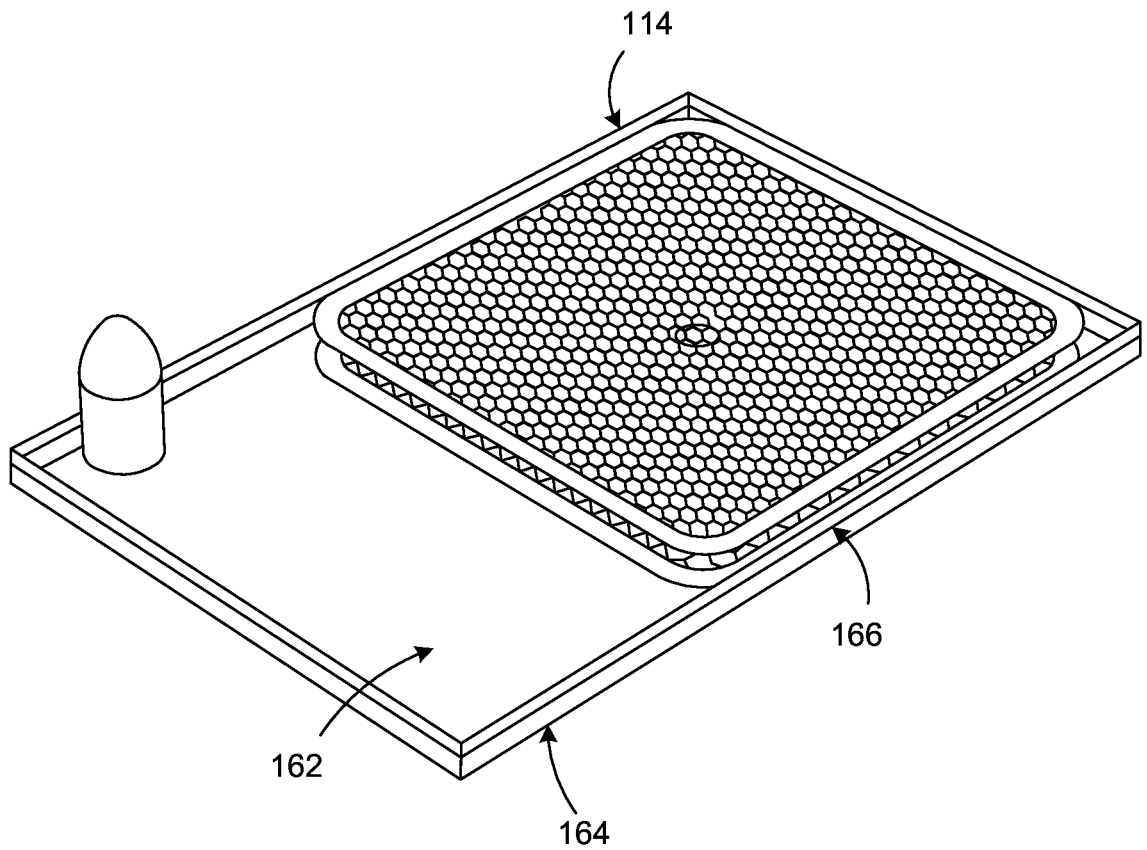
FIG. 15 is a perspective view of the phototherapy light source of the phototherapy system illustrated in FIG. 11.
Figure 16:
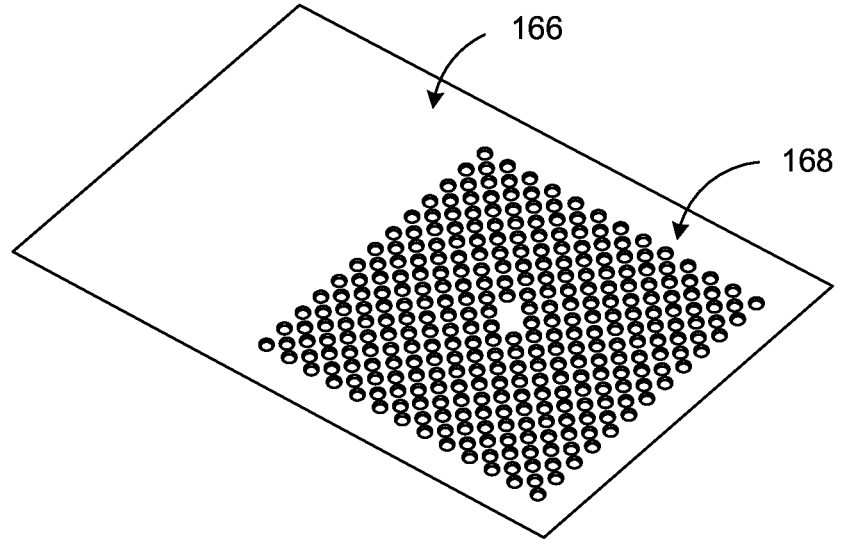
FIG. 16 is a perspective view of the lamp of the phototherapy system illustrated in FIG. 11.

As shown in FIG. 6, the second portion 24 of the handle 12 has a first end 42, a second end 44, a first side 46, a second side 48, a top surface 50, a bottom surface 52, and a main body 54 that defines a first recess 56, a second recess 58, and an opening 60. The first recess 56 extends from the bottom surface 52 toward the top surface 50 and is sized and configured to house a portion of the phototherapy light source 14 and any other components considered suitable to utilize with a phototherapy system. The second recess 58 extends from the bottom surface 52 toward the top surface 50, around a portion of the inside perimeter of the main body 54, and is sized and configured to receive the projection 40 defined by the first portion 22 of the handle 12 such that a snap-fit attachment can be accomplished between the first and second portions 22, 24 of the handle 12. The opening 60 is defined on the second end 44 and extends from the second end 44 toward the first end 42 to the first recess 56. The opening 60 is sized and configured to receive a portion of the phototherapy light source 14. The handle 12 provides structure for a patient to grasp the phototherapy system 10 during use, as described in more detail herein. Various features, components, devices, and/or systems can be housed within the handle 12 and/or attached to the handle 12, the phototherapy light source 14, the camera 16, and/or the positioning sensor 18 to accomplish use of the phototherapy system 10, as described herein. Examples of features, components, devices and/or systems that can be housing within a handle and/or attached to a handle, a phototherapy light source, a camera, and/or a positioning sensor include one or more batteries, microcontrollers, microcontrollers with wireless (e.g., Bluetooth connectivity), battery charging circuits, inductive charging coils, electrical connection ports (e.g., USB C), drive circuitry for a lamp (e.g., plasma lamp, LED lamp), and any other feature, component, device, and/or system considered suitable for a particular embodiment.

While the handle 12 has been illustrated as having a particular structural arrangement and as having first and second portions 22, 24 releasably attached to one another using a snap-fit attachment, a handle can have any suitable structural arrangement and utilize any suitable type of attachment. Selection of a suitable structural arrangement for a handle and of a suitable type of attachment between first and second portions of a handle can be based on various considerations, including the structural arrangement of a light source intended to be attached to the handle. Examples of techniques and methods of attachment considered suitable to utilize between a first portion of a housing and a second portion of a housing include using threaded connections, snap-fit attachments, using one or more connectors, one or more mating slots and projections, adhesives, and any other technique or method of attachment considered suitable for a particular embodiment. In an alternative embodiment, a handle can be formed as a single, unitary piece of material.

The phototherapy light source 14 is attached to the handle 12, has an on state when the phototherapy system is in the second, active state, has an off state when the phototherapy system is in the first, deactivated state, and is adapted to emit a light in a therapeutic wavelength. In the illustrated embodiment, the phototherapy light source 14 has a first sheet of transparent material 62, a second sheet of transparent material 64, and a lamp 66 disposed between the first and second sheets of transparent material 62, 64. Each sheet of transparent material can be formed of any suitable material, such as quartz, glass, and other transparent materials, and can include one or more conductive films or foil patterns. The transparent sheets of material can comprise the same or different materials. Quartz is considered particularly advantageous for the sheets of transparent material at least because of its ready availability, symmetrical molecular structure, relative hardness as compared to glass, and other considerations. Thus, it is considered particularly advantageous that at least one of the first and second sheets of transparent material comprises quartz. Furthermore, it is considered particularly advantageous that each of the first and second sheets of transparent material comprises quartz. When in the on state, the phototherapy light source 14 emits light that includes phototherapeutic component wavelengths. When in the off state, the light source 14 does not emit light that includes phototherapeutic component wavelengths.

Any suitable phototherapy light source can be included in a phototherapy system and selection of a suitable phototherapy light source can be based on various considerations, including the intended use of the phototherapy system of which the phototherapy light source is a component. Examples of phototherapy light sources considered suitable for inclusion in a phototherapy system include those that include a structure for supporting a lamp, such as first and second sheets of transparent material, those that include a plasma lamp, a gas filled plasma lamp filled with XeCL, a plurality of LEDs, a flat panel lamp, a fluorescent lamp, a combination of lamps, such as those described herein, and any other phototherapy light source considered suitable for a particular embodiment. In the illustrated embodiment, the lamp 66 comprises a gas filled plasma lamp 68 filled with XeCL.

A lamp included in a phototherapy system can have any suitable output and emit light in any suitable therapeutic wavelength and selection of a suitable output and of a suitable wavelength can be based on various considerations, such as the treatment intended to be performed by the phototherapy system of which the lamp is a component. Examples of outputs considered suitable for a lamp include outputs of about 3 mW/cm$^2$, about 16 mW/cm$^2$, about 20 mW/cm$^2$, between about 3 mW/cm$^2$ and about 21 W/cm$^2$, between about 15 mW/cm$^2$ and about 21 mW/cm$^2$, between about 3 mW/cm$^2$ and about 50 mW/cm$^2$, about 50 mW/cm$^2$, and any other output considered suitable for a particular embodiment. An output of between about 15 mW/cm$^2$ and about 21 mW/cm$^2$ is considered particularly advantageous at least because it allows for relatively brief treatment times while representing an attractive output level for usage without the need for additional precautions, training, personnel and/or equipment. In this regard, an output of about 16 mW/cm$^2$ is considered particularly advantageous. An output of about 20 mW/cm$^2$ is also considered particularly advantageous in this regard. Examples of therapeutic wavelengths considered suitable for a lamp to emit include visible wavelengths, UV wavelengths, UVB wavelengths, UVB wavelengths between about 300 nanometers and about 320 nanometers, UVB wavelengths about 308 nanometers, and any other wavelength considered suitable for a particular embodiment. In one particular example, the plasma lamp 68 has an output of about 20 mW/cm² and emits light in a UVB wavelength of about 308 nanometers. In another example, the plasma lamp 68 has an output of about 16 mW/cm² and emits light in a UVB wavelength of about 308 nanometers.

While a single lamp 66 has been illustrated as included in the phototherapy light source, a phototherapy light source can include any suitable number of lamps and selection of a suitable number of lamps to include in a phototherapy light source can be based on various considerations, including the treatment intended to be completed using the phototherapy system. Examples of numbers of lamps considered suitable to include in a phototherapy light source include one, at least one, two, a plurality, three, four, five, more than five, and any other number considered suitable for a particular embodiment.

In the illustrated embodiment, the camera 16 is attached to the phototherapy light source 14 and provides a mechanism for acquiring one or more images of a treatment site during use. The camera 16 is positioned on the phototherapy light source 14 at about the center of the portion of the first sheet of transparent material 62 that is disposed outside of the handle 12 and is directed towards an axis 69 that extends through a portion of the top surface of the 34 of the first portion 22 of the handle 12. While a single camera 16 has been illustrated as attached to the phototherapy light source 14 at a particular location, any suitable type and number of cameras can be positioned at any suitable location on a phototherapy system. Selection of a suitable type and number of cameras to include in a phototherapy system, and of a suitable location to position a camera on a phototherapy system, can be based on various considerations, such as the intended use of the phototherapy system. Examples of numbers of cameras considered suitable to include in a phototherapy system include one, at least one, two, a plurality, three, four, more than four, and any other number considered suitable for a particular embodiment. Examples of locations considered suitable to position a camera include at, near, adjacent, or about the center of a sheet of transparent material (e.g., first sheet of transparent material, second sheet of transparent material), adjacent a handle, adjacent an end of a sheet of transparent material, between an end of a sheet of transparent material and the center of the sheet of transparent material, on a handle, and any other location considered suitable for a particular embodiment. Examples of cameras considered suitable to include in a phototherapy system include cameras that utilize CMOS active-pixel image sensors, cameras that utilize infrared (IR) technology (e.g., this technology may illustrate the existence of lesions), cameras that detect ultra-violet (UV) fluorescence (e.g., UV light can be used as a Wood's lamp to diagnose skin conditions), and any other camera considered suitable for a particular embodiment.

In the illustrated embodiment, the positioning sensor 18 is attached to the handle 12 and provides a mechanism for acquiring the position of the phototherapy system 10 during use. The positioning sensor 18 is positioned on the handle 12 at about the center of the second end of the first portion 22 of the handle 12. While a single positioning sensor 18 has been illustrated as attached to the handle 12 at a particular location, any suitable type and number of positioning sensors can be positioned at any suitable location on a phototherapy system. Selection of a suitable type and number of positioning sensors to include in a phototherapy system, and of a suitable location to position a positioning sensor on a phototherapy system, can be based on various considerations, such as the intended use of the phototherapy system. Examples of numbers of positioning sensors considered suitable to include in a phototherapy system include one, at least one, two, a plurality, three, four, more than four, and any other number considered suitable for a particular embodiment. Examples of locations considered suitable to position a positioning sensor include at, near, adjacent, or about the center of an end of a portion of a handle, adjacent a main body of a handle, centrally located within a recess defined by a handle, and any other location considered suitable for a particular embodiment. Examples of positioning sensors considered suitable to include in a phototherapy system include multiple axis accelerometers, and any other positioning sensor considered suitable for a particular embodiment. Alternative to, or in combination with, including a positioning sensor, a phototherapy system can include one or more proximity sensors to detect the distance the phototherapy system is relative to a point of treatment, or other portion of a body.

In an alternative embodiment, a phototherapy system can include a handle that does not house any features, components, devices, and/or systems and that alternatively includes a cord attached to the handle at one end and attached to a base housing at a second end. The base housing can house one or more features, components, devices, and/or systems, such as those described herein as being housing by the handle 12.

FIGS. 11, 12, 13, 14, 15, and 16 illustrate another example phototherapy system 110. The phototherapy system 110 is similar to the phototherapy system 10 illustrated in FIGS. 1, 2, 3, 4, 5, 6, 7, 8, 9, and 10 and described above, except as detailed below. The phototherapy system 110 has a handle 112, a phototherapy light source 114, a camera 116, and a positioning sensor 118.

The phototherapy light source 114 is attached to the handle 112, has an on state and an off state, and is adapted to emit a light in a therapeutic wavelength. In the illustrated embodiment, the phototherapy light source 114 has a first sheet of transparent material 162, a second sheet of transparent material 164, and a lamp 166 disposed between the first and second sheets of transparent material 162, 164. When in the on state, the phototherapy light source 114 emits light that includes phototherapeutic component wavelengths. When in the off state, the light source 114 does not emit light that includes phototherapeutic component wavelengths.

In the illustrated embodiment, the lamp 166 comprises a plurality of LEDs 168. Each LED of the plurality of LEDs 168 has a predetermined treatment time when the phototherapy light source 114 is moved from the off state to the on state and a selected treatment is being performed. A predetermined treatment time can be based upon the characteristics of an LED of the plurality of LEDs of which the predetermined treatment time is being associated, as described in more detail herein. The characteristics can be obtained by completing a spectral analysis of each LED of the plurality of LEDs. The process of associating a predetermined treatment time to each LED of the plurality of LEDs for a selected treatment results in a phototherapy system that is customized relative to the specific components included in the system. A plurality of LEDs included in a phototherapy system can be positioned in any suitable configuration, such as a rectangular grid, and spacing of each LED relative to another LED can be based on various considerations, such as whether each LED includes optics and/or each LED's wattage.

An LED of a plurality of LEDs can have any suitable predetermined treatment time and can be based on various characteristics of the LED, such as the color temperature, output, voltage, and any other characteristic of an LED. Examples of predetermined treatment times considered suitable for an LED of a plurality of LEDs include those in which a first LED of a plurality of LEDs has a first predetermined treatment time and a second LED of the plurality of LEDs has a second predetermined treatment time that is different than the first predetermined treatment time, a first LED of a plurality of LEDs has a first predetermined treatment time, a second LED of the plurality of LEDs has a second predetermined treatment time, a third LED of a plurality of LEDs has a third predetermined treatment time that is different than the first predetermined treatment time and the second first predetermined treatment time, a first LED of a plurality of LEDs has a first predetermined treatment time and a second LED of the plurality of LEDs has a second predetermined treatment time that is greater than the first predetermined treatment time, a first LED of a plurality of LEDs has a first predetermined treatment time, a second LED of the plurality of LEDs has a second predetermined treatment time, a third LED of a plurality of LEDs has a third predetermined treatment time that is greater than the first predetermined treatment time and the second first predetermined treatment time, a first LED of a plurality of LEDs has a first predetermined treatment time and a second LED of the plurality of LEDs has a second predetermined treatment time that is less than the first predetermined treatment time, a first LED of a plurality of LEDs has a first predetermined treatment time, a second LED of the plurality of LEDs has a second predetermined treatment time, a third LED of a plurality of LEDs has a third predetermined treatment time that is less than the first predetermined treatment time and the second first predetermined treatment time, a first LED of a plurality of LEDs has a first predetermined treatment time, a second LED of the plurality of LEDs has a second predetermined treatment time, a third LED of a plurality of LEDs has a third predetermined treatment time that is greater than the first predetermined treatment time and less than the second first predetermined treatment time, a first LED of a plurality of LEDs has a first predetermined treatment time, a second LED of the plurality of LEDs has a second predetermined treatment time, a third LED of a plurality of LEDs has a third predetermined treatment time that is less than the first predetermined treatment time and greater than the second first predetermined treatment time, and any other predetermined treatment time considered suitable for a particular embodiment. In the illustrated embodiment, each LED of the plurality of LEDs has an output of about 16 mW/cm$^2$ and emits light in a UVB wavelength of about 310 nanometers.

The phototherapy systems and methods of using a phototherapy system described herein can be used to treat a number of dermatologic conditions monotherapeutically (e.g., using only a phototherapy system, such as those described herein) or using a combination of a phototherapy system and one or more oral drugs and/or topical drugs. Examples of dermatologic conditions considered suitable to treat with the phototherapy systems and methods of using a phototherapy system described herein include psoriasis, vitiligo, eczema, and any other dermatologic condition considered suitable to treat with the phototherapy systems and methods described herein.

Various methods of using a phototherapy system and methods of manufacturing a phototherapy system are described herein. While the methods described herein are shown and described as a series of acts, it is to be understood and appreciated that the methods are not limited by the order of acts, as some acts may in accordance with these methods, occur in the order shown and/or described, in different orders, and/or concurrently with other acts described herein.

Figure 17:
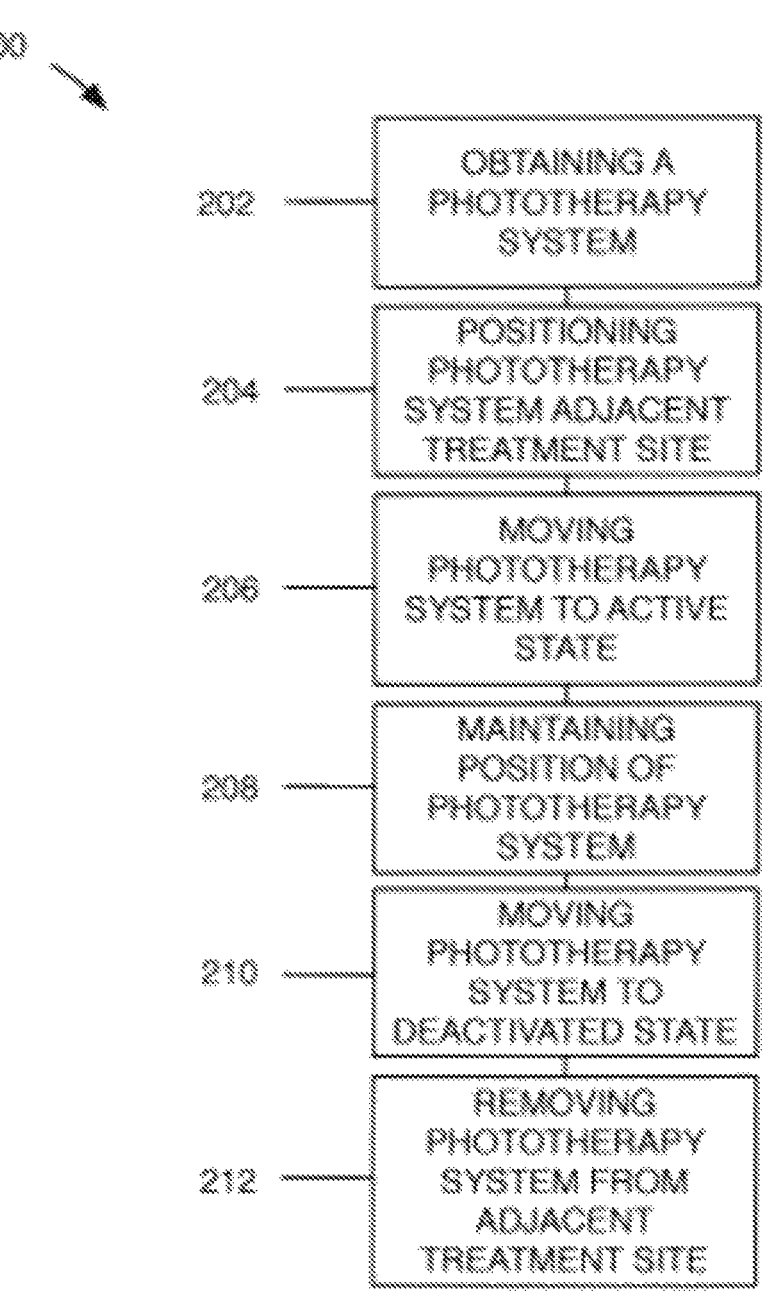
FIG. 17 is a schematic illustration of an example method of using a phototherapy system.

FIG. 17 illustrates a schematic illustration of an example method 200 of using a phototherapy system.

An initial step 202 comprises obtaining a phototherapy system. Another step 204 comprises positioning the phototherapy system adjacent a treatment site. Another step 206 comprises moving the phototherapy system from a first, deactivated state to a second, active state. Another step 208 comprises maintaining the position of the phototherapy system adjacent the treatment site for a period of time. Another step 210 comprises moving the phototherapy system from the second, active state to the first, deactivated state. Another step 212 comprises removing the phototherapy system from adjacent the treatment site.

Step 202 can be accomplished using any suitable phototherapy system and selection of a suitable phototherapy system can be based on various considerations, including the treatment intended to be completed with the phototherapy system. Examples of phototherapy systems considered suitable to complete a method of using a phototherapy system include phototherapy system 10, phototherapy system 110, phototherapy systems manufactured using the methods of manufacturing a phototherapy system described herein, combinations of the phototherapy systems described herein, and any other phototherapy system considered suitable for a particular embodiment.

An optional step 202A that can be completed prior, or subsequent, to step 202 comprises pairing the phototherapy system to an application (e.g., web-based application, mobile application). Another optional step 202B that can be completed subsequent to optional step 202A comprises customizing the application to a specific patient such that the application, and associated use of the phototherapy system, is patient specific. Optional step 202B can be accomplished by a physician, or other medical specialist, inputting patient data into the application that relates to the patient (e.g., type of treatment to be completed, location of treatment site, treatment time, period of time to pass between treatments). Optionally, an application can include information relating to required maintenance of the phototherapy system (e.g., maintenance dates) and remind the patient of such required maintenance and/or include treatment instructions that can be reviewed or provided to a patient. Optionally, an application can be in communication with a camera and/or positioning sensor of a phototherapy system such that precise treatment can be achieved. For example, data relating to the position of the phototherapy system can be provided to the application via a camera and/or positioning sensor and compared to the patient data provided by the physician. Various notifications can be provided to the patient based on the comparison of the data relating to the position of the phototherapy system and the data provided by the physician. For example, if the phototherapy system is not placed at the proper treatment site, the application can notify the patient to reposition the phototherapy system. Alternatively, if the phototherapy system has been at the treatment site for a predetermined treatment time, the application can notify the patient that it is time to deactivate the phototherapy system or the application can send instructions to the phototherapy system to move it to the first, deactivated state. Optionally, one more sensors can be used to monitor light output and adjust either treatment time or output of the light source to provide a desired treatment. An application can also provide other notifications or controls to a phototherapy system. For example, an application can prevent a phototherapy system from being moved from a first, deactivated state to a second, active state if a specified period of time has not elapsed between treatments. Alternatively, or in combination with the previous example, an application can inquire as to the outcome of a previous treatment or current status of a treatment site from a patient (e.g., is the treatment site red, is the treatment site painful) and, based on the data provided by the patient, prevent a phototherapy system from being moved from a first, deactivated state to a second, active state or allow treatment to continue as defined by the physician. Optionally, an application can transmit data input by the patient and/or obtained during treatment to the physician such that the physician can update treatment based on the transmitted data. For example, initial treatments are generally accomplished at a lower dose (e.g., 1000 mJ) to prevent complications. Therefore, the receipt of data by the physician regarding completed treatments allows the physician to increase the dose (e.g., to 3000 mJ) based on the transmitted data.

Step 204 can be accomplished by applying a force on the phototherapy system directed toward a treatment site until the phototherapy system is positioned adjacent the treatment site.

Step 206 can be accomplished using a switch attached to the phototherapy system, remotely via an application in communication with the phototherapy system, or using any other suitable mechanism for activating a phototherapy system.

Step 208 can be accomplished by maintaining the position of the phototherapy system adjacent the treatment site for any suitable period of time. Examples of suitable periods of time include one or more seconds, minutes, hours, and any other period of time considered suitable for a particular treatment.

Step 210 can be accomplished using a switch attached to the phototherapy system, remotely via an application in communication with the phototherapy system, or using any other suitable mechanism for deactivating a phototherapy system.

Step 212 can be accomplished by applying a force on the phototherapy system directed away from the treatment site until the phototherapy system has been removed from adjacent the treatment site.

Figure 18:
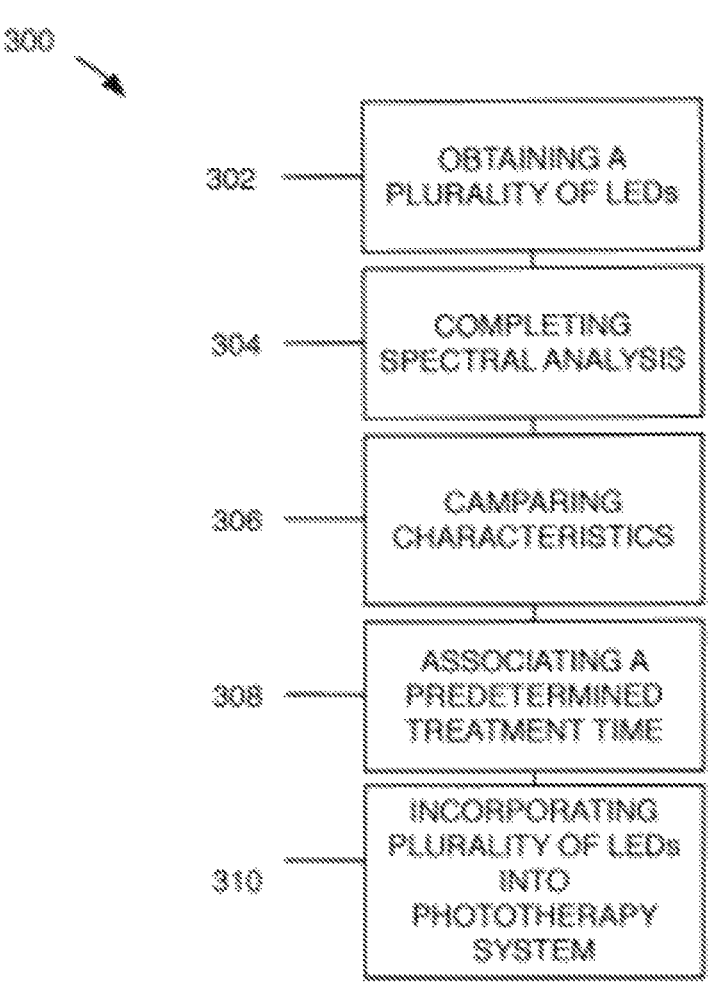
FIG. 18 is a schematic illustration of an example method of manufacturing a phototherapy system.

FIG. 18 illustrates a schematic illustration of an example method 300 of manufacturing a phototherapy system. The method 300 of manufacturing a phototherapy system provides a mechanism for customizing a plurality of LEDs such that predetermined treatment times are associated with each LED of the plurality of LEDs when the phototherapy system is in the second, active state. The predetermined treatment times are based upon one or more characteristics of each LED of the plurality of LEDs, such as color temperature, output, voltage, and other characteristics, obtained through spectral analysis. Therefore, the characteristic can be selected from the group consisting of a color temperature, an output, and a voltage. The method 300 of manufacturing a phototherapy system prevents inaccurate treatment, accounts for a variation in intensity of the LEDs in a plurality of LEDs, and increases the efficiency of the phototherapy system by addressing the binning process that is completed when LEDs are manufactured. The method 300 of associating a predetermined treatment time to each LED of the plurality of LEDs for a selected treatment results in a phototherapy system that is customized relative to the specific components included in the system.

An initial step 302 comprises obtaining a plurality of LEDs. Another step 304 comprises completing a spectral analysis of each LED of the plurality of LEDs to obtain characteristics of each LED of the plurality of LEDs. Another step 306 comprises comparing the characteristics of each LED of the plurality of LEDs and the characteristics required of an LED for a treatment intended to be performed. Another step 308 comprises associating a predetermined treatment time to each LED of the plurality of LEDs based on the comparison of the characteristics of each LED of the plurality of LEDs and the characteristics required of an LED for a treatment intended to be performed. Another step 310 comprises incorporating the plurality of LEDs into a phototherapy system.

Step 302 can be accomplished using any suitable type of LED and selection of a suitable type of LED can be based on various considerations, including the treatment intended to be completed with a phototherapy system of which an LED is included. Examples of LEDs considered suitable to include in a phototherapy system include those described herein.

Step 304 provides a mechanism for accounting for variances in spectral output and/or optical power of each LED within a plurality of LEDs. For example, if the LEDs within a plurality of LEDs have significant variances in spectral output or optical power, providing uniform erythemal or biological effective doses can be ensured by scanning each LED and programming the drive circuitry to run each LED with a weighted factor, such that each portion of the treatment area receives an effective does without over or under-dosing other portions of the treatment area.

Step 308 can be accomplished by configuring the phototherapy system such that when the phototherapy system is moved from the first, deactivated state to the second, active state each LED of the plurality of LEDs moves from the off state to the on state simultaneously and each LED of the plurality of LEDs is moved from the on state to the off state independent of the state of the remaining LEDs of the plurality of LEDs. Alternatively, step 308 can be accomplished by configuring the phototherapy system such that when the phototherapy system is moved from the first, deactivated state to the second, active state each LED of the plurality of LEDs moves from the off state to the on state independent of the state of the remaining LEDs of the plurality of LEDs and is moved from the on state to the off state independent of state of the remaining LEDs of the plurality of LEDs. Each LED of the plurality of LEDs can have a predetermined treatment time that varies relative to the remaining LEDs of the plurality of LEDs.

Step 310 can be accomplished by positioning the plurality of LEDs on a phototherapy light source, such as phototherapy light source 114.

An optional step that can be included in method 300 comprises using the phototherapy system. This optional step can be accomplished as described herein with respect to method 200.

Those with ordinary skill in the art will appreciate that various modifications and alternatives for the described and illustrated embodiments can be developed in light of the overall teachings of the disclosure, and that the various elements and features of one example described and illustrated herein can be combined with various elements and features of another example without departing from the scope of the invention. For example, the application of the sensor elements and control features to areas related to localized photography, such as cosmetic or aesthetic devices (e.g., hair combs, hair dryers, and the like) falls within the scope of this disclosure. Accordingly, the particular examples disclosed herein have been selected by the inventor(s) simply to describe and illustrate examples of the invention and are not intended to limit the scope of the invention or its protection, which is to be given the full breadth of the appended claims and any and all equivalents thereof.

What is claimed is:

1. A phototherapy system having a first, deactivated state and a second, activated state, the phototherapy system comprising:

a handle having a first portion and a second portion, the first portion defining a first recess and a first opening, and the second portion defining a second recess and a second opening; and a phototherapy light source attached to the handle and adapted to emit a light in a therapeutic wavelength, the phototherapy light source including first and second sheets of transparent material, each of the first and second sheets of transparent material disposed through one of the first and second openings and extending from the handle, the phototherapy light source having an on state and an off state and comprising a plurality of light emitting diodes, each light emitting diode of the plurality of light emitting diodes having an on state and an off state;

wherein the plurality of light emitting diodes is disposed between the first and second sheets of transparent material; and wherein the phototherapy system is configured such that each light emitting diode of the plurality of light emitting diodes moves from the on state to the off state simultaneously when the phototherapy system is moved from the first, deactivated state to the second, activated state and such that each light emitting diode of the plurality of light emitting diodes moves from the on state to the off state independently of the state of the remaining light emitting diodes of the plurality of light emitting diodes when the phototherapy system is moved from the second, activated state to the first, deactivated state.

2. The phototherapy system of claim 1, wherein a first light emitting diode of the plurality of light emitting diodes has a first predetermined treatment time; and wherein a second light emitting diode of the plurality of light emitting diodes has a second predetermined treatment time that is different than the first predetermined treatment time.

3. The phototherapy system of claim 1, wherein a characteristic of each light emitting diode of the plurality of light emitting diodes is selected from a group consisting of a color temperature, an output, and a voltage.

4. The phototherapy system of claim 1, wherein the phototherapy light source is adapted to have an output of 16 mW/cm$^2$.

5. The phototherapy system of claim 1, wherein the therapeutic wavelength is a UVB wavelength.

6. The phototherapy system of claim 5, wherein the UVB wavelength is between 300 nanometers and 320 nanometers.

7. The phototherapy system of claim 5, wherein the UVB wavelength is 308 nanometers.

8. The phototherapy system of claim 1, wherein at least one of the first and second sheets of transparent materials comprises quartz.

9. The phototherapy system of claim 1, wherein each of the first and second sheets of transparent material comprises quartz.

10. The phototherapy system of claim 1, wherein the phototherapy light source is adapted to emit a light in only the therapeutic wavelength.

11. The phototherapy system of claim 1, further comprising a camera attached to the phototherapy light source.

12. The phototherapy system of claim 11, wherein the camera is positioned at the center of the first sheet of transparent material.

13. The phototherapy system of claim 1, further comprising a positioning sensor attached to the handle.

14. The phototherapy system of claim 1, further comprising a lamp comprising the plurality of light emitting diodes.

15. The phototherapy system of claim 14, wherein the lamp is disposed between the first sheet of transparent material and the second sheet of transparent material.

16. The phototherapy system of claim 15, wherein at least one of the first sheet of transparent material and the second sheet of transparent material comprises quartz.

* * * * *